United States Patent [19]

Ujimoto et al.

[11] Patent Number: 5,091,039
[45] Date of Patent: Feb. 25, 1992

[54] METHOD AND APPARATUS FOR APPLYING ELASTIC BAND ONTO MOVING WEB

[75] Inventors: Hiroshi Ujimoto, Kawanoe; Hironori Nomura, Iyomishima; Taiji Shimakawa, Kawanoe; Junji Shinohara, Iyomishima; Shigetoyo Kobayashi, Kagawa; Hiroki Yamamoto, Kawanoe, all of Japan

[73] Assignee: Uni-Charm Corporation, Ehime, Japan

[21] Appl. No.: 499,007

[22] Filed: Mar. 26, 1990

Related U.S. Application Data

[62] Division of Ser. No. 231,537, Aug. 12, 1988, abandoned.

[30] Foreign Application Priority Data

Aug. 18, 1987 [JP] Japan .................. 62-206157

[51] Int. Cl.⁵ .................................. B32B 31/00
[52] U.S. Cl. ........................... 156/519; 156/164; 156/552
[58] Field of Search ............ 156/164, 265, 495, 496, 156/517, 519, 552

[56] References Cited

U.S. PATENT DOCUMENTS

| | | | |
|---|---|---|---|
| 3,963,557 | 6/1976 | Patterson | 156/568 |
| 4,578,133 | 3/1986 | Oshefsky et al. | 156/164 |
| 4,608,115 | 8/1986 | Schroth et al. | 156/164 |
| 4,610,751 | 9/1986 | Eschler | 156/517 |
| 4,675,068 | 6/1987 | Lundmark | 156/164 |
| 4,726,876 | 2/1988 | Tomsovic | 156/552 |
| 4,801,345 | 1/1989 | Dussaud et al. | 156/164 |
| 4,863,542 | 9/1989 | Oshefsky et al. | 156/552 |
| 4,909,885 | 3/1990 | Swenson | 156/521 |
| 4,915,767 | 4/1990 | Rajala et al. | 156/164 |

Primary Examiner—Michael W. Ball
Assistant Examiner—Steven D. Maki
Attorney, Agent, or Firm—Fred Philpitt

[57] ABSTRACT

The present invention generally resides in method and apparatus for intermittently applying pieces of elastic band severed into a predetermined length onto a moving continuous web at predetermined positions. The apparatus comprising elastic band transfer means including a plurality of independently rotatable rotor elements coaxially supported in rotatable fashion and carrying on respective arc-shaped outer surfaces suction members wherein the respective rotor elements carrying the respective suction members are adapted to be rotated along common circumferential path and the respective rotor elements are coupled to a drive wheel eccentrically located relative to a rotational center of the respective rotor elements and adapted to be rotated at a constant speed by a rotatable slider crank mechanism; suction distributor means for the respective suction members, adapted to operate synchronously with rotation of the drive wheel; means to feed continuous elastic band tangentially to the circumferential path of the respective suction members; means intermittently cooperating with one of the respective suction members periodically advanced by the elastic band transfer means to a predetermined position to sever the continuous elastic band; and web feeding means located in opposition to an end position of transport of the severed piece of elastic band along the circumferential path so that the piece of elastic band may be effectively transferred onto the web. This apparatus may further comprise means by which at least one ends of the respective suction members are pivotally supported by the respective rotor elements in laterally displaceable fashion so that the one ends are laterally displaced as the respective rotor elements rotate.

4 Claims, 8 Drawing Sheets

METHOD AND APPARATUS FOR APPLYING ELASTIC BAND ONTO MOVING WEB

This is a division of application Ser. No. 231,537, filed Aug. 12, 1988, now abandoned, and the benefits of 35 USC 120 are claimed relative to it.

BACKGROUND OF THE INVENTION

The present invention relates to method and apparatus for applying an elastic band onto a moving web and more particularly to method and apparatus for intermittently applying pieces of elastic band severed into a predetermined lengths, at least partially displacing said pieces laterally of the direction in which said web travels, onto said web thus continuously forming a plurality of articles which can to be severed into said individual articles. This method and apparatus can be used as an effective technique for applying elastic band onto various garments such as disposable diapers, diaper-covers and training pants.

For garments such as disposable diapers, various techniques are already been known for applying an elastic band onto the openings surrounding the legs and waist of the user for fitness.

Japanese Patent Publication No. 57-26219 discloses a technique such that a continuous elastic band is applied with adhesive at regular intervals along its longitudinal direction while said continuous elastic band is maintained in a stretched condition, said continuous elastic band being bonded onto said continuous web with said adhesive, said continuous elastic band being severed at non-bonded portions that are not applied with adhesive and at the same time said non-bonded portions are allowed to contract so as to make these portions non-functional, and thereby said elastic band is intermittently bonded onto said web. According to this technique of the prior art, however, said non-functional portions are wasteful and, in addition, said non-bonded portions are left to contract inwardly after the elastic band has been bonded onto the web, and this contraction of said non-bonded portions forms undesirable openings at the ends of the finished article through which leakage of excretion occurs.

Japanese Disclosure Gazette No. 58-174603 discloses a technique in which a continuous elastic band is applied with adhesive at regular intervals along its longitudinal direction while said continuous elastic band is maintained in a stretched condition, said continuous elastic band being fed onto the peripheral surface of a rotatable suction drum, said continuous elastic band being severed at portions applied with no adhesive and at the same time the portions with no adhesive applied are left contract to make these portions non-functional, then this discontinuous elastic band is transferred onto the continuous web and thereby said elastic bend is intermittently bonded onto said web. This technique certainly avoids the formation of undesirable openings at the ends of the finished article but the problem of waste remains unsolved.

Japanese Disclosure Gazette No. 58-180601 discloses a technique wherein a continuous elastic band is continuously or intermittently applied with adhesive and then fed onto the peripheral surface of a rotatable suction drum, said elastic band being severed on said rotatable suction drum into predetermined lengths, each severed piece of elastic band is held on said peripheral surface of said rotatable suction drum, each piece of elastic band is moved along with said peripheral surface but the following continuous elastic band is made to slide relative to said peripheral surface so that the rear end of said severed piece of elastic band is spaced from the front end of the following continuous elastic band, then said severed piece of elastic band is held on said peripheral surface of the rotatable suction drum and moved along with said peripheral surface but the following continuous elastic band is made to slide relative to said peripheral surface so as to space the rear end of said severed piece of elastic band from the front end of said following continuous elastic band, then said severed piece of elastic band is transferred onto said web, and thereby said elastic band is intermittently bonded onto said web. According to this technique, however, a control of said slippage and a suction pressure inevitably involves unreliable technical factors even though said formation of undesirable openings due to contraction of the non-bonded portions at the ends of the finished article can be avoided and the intermittent application of adhesive onto the continuous elastic band is not required. In view of such limitations, this technique of the prior art is not suitable for bonding the continuous elastic band onto said web at a high rotational speed.

A technique for bonding the elastic band onto the web so that the individually severed pieces of said elastic band have predetermined curved orientations on said web is well known, for example, from Japanese Disclosure Gazette No. 61-162462. However, according to this technique, mechanisms constituting the respective means to space the respective severed pieces of elastic bands from one another on the rotatable device, to hold said elastic band, to displace said elastic band laterally of the direction in which the web travels and to transfer said pieces of elastic band are so complicated that this technique is not suitable for bonding the elastic band onto the web in view of speed, reliability and efficiency of the various mechanisms included in the apparatus.

Accordingly, a primary object of the present invention is to provide a technique for intermittently bonding elastic band onto a web at predetermined positions at high speed, reliability and efficiency through a continuous operation including the step of holding said elastic band, particularly holding said elastic band while at least partially displaced laterally of the web, if desired, so as to apply said elastic band onto said web in such orientation.

SUMMARY OF THE INVENTION

According to the present invention, the object as set forth above is achieved by following a method and apparatus for intermittently applying pieces of elastic band severed into predetermined lengths onto a moving continuous web at predetermined positions:

Method comprising steps of feeding a continuous elastic band to a a location for applying said pieces of elastic band onto said web; circumferentially holding and transferring said elastic band and severing it into predetermined lengths during said process for applying; accelerating the transfer of a preceding piece of elastic band to produce a spacing between said preceding piece of elastic band and the following elastic band while maintaining a circumferential path for the elastic band, prior to being fed to a position at which said preceding piece of elastic band comes into tangential contact with said web; and successively transferring said elastic band from one end thereof onto said web at a predetermined position in synchronization with the speed at which said web is fed to said position of tangential contact.

In a preferred embodiment said method further comprises laterally displacing at least a part of said severed piece of elastic band during transport of said elastic band.

Apparatus comprising elastic band transfer means including a plurality of independently rotatable rotor elements coaxially supported in rotatable manner and carrying on respective arc-shaped outer peripheries suction members wherein said respective rotor elements carrying said respective suction members are adapted to be rotated along a common rotational orbit and said respective rotor elements are coupled to a drive wheel eccentrically located relative to a rotational center of said respective rotor elements and adapted to be rotated at a constant speed by a rotatable slider crank mechanism; suction distributor means for said respective suction members, adapted to operate synchronously with rotation of said drive wheel; means to feed continuous elastic band tangentially to said circumferential path of said respective suction members., means intermittently co-operating with said respective suction members periodically advanced by said elastic band transfer means to a predetermined position to sever said continuous elastic band into a predetermined length; and web feeding means located in opposition to an end position on said circumferential path along which said severed piece of elastic band is transported so that said piece of elastic band may be effectively transferred onto said web.

In a preferred embodiment, said apparatus further comprises means for pivotally supporting at least one end of each said suction member on the associated rotor element in a laterally displaceable manner so that said one end may be laterally displaced as said associated rotor element is rotated.

In a preferred embodiment, the piece of elastic band severed into a predetermined length is continuously transported along a circumferential path while said piece of elastic band is maintained in stretched condition. The severed piece of elastic band is accelerated along the circumferential path and, when it reaches the position at which the web comes into tangential contact with said piece of elastic band, the rear end of said piece is spaced from the following elastic band and at least a part of said piece is laterally displaced. Such spacing may be preset to correspond to a spacing between each pair of adjacent pieces of elastic band applied onto the web continuously fed to said position in order to ensure that the severed pieces of elastic band can be successively applied onto the web at predetermined positions and in the laterally displaced orientation while both the continuous elastic band and the continuous web are continuously fed.

In the apparatus to perform the above-mentioned method of the present invention, the elastic band transfer means including the drive wheel having an eccentric rotational center and a plurality of independently rotatable rotor elements are controlled by the rotatable slider crank mechanism (see FIG. 9) connecting said drive wheel to said elastic band transfer means. The drive wheel and the respective rotor elements coupled by the rotatable slider crank mechanism define between their respective rotational centers O, O' a stationary link A. A link B extending from the drive wheel and a link D comprising guide grooves into which sliders C of the respective rotor elements are slidably engaged serve as a crank. The link D moves to positions (1), (2), (3), ... as the rotation of the drive wheel at a constant speed moves the link B to positions (1)', (2)', (3)', ... . During such movement, the length of the link D progressively increases over the arc of the movement path (1)(2) ... (4)(5) and progressively decreases over the arc (5)(6) ... (8)(1), so the link D moves at a variable speed while the link B moves at a constant speed. Accordingly, the respective rotor elements serving as the slider C rotate at a variable speed. The suction members mounted on the arc-shaped outer surfaces of the respective rotor elements successively hold under suction effect the continuous elastic band as being maintained in stretched condition while said continuous elastic band is fed to said suction members (the elastic band transfer means) adjacent a point at which the respective rotor elements rotate at the lowest speed (adjacent the position (1)), and rotate together with the elastic band held thereon. Then the respective rotor elements are progressively accelerated from the position (1) to the position (5) and a spacing between each pair of adjacent rotor elements progressively increases. Immediately before each pair of adjacent rotor elements comes again closest to each other, a cutter knife adapted to operate in synchronously with the rotor elements severs the continuous elastic band into a predetermined length corresponding to a length held on each suction member carried by each rotor elements. When the rotor element independently holding said severed piece of elastic band is accelerated to the highest speed (adjacent the position (5)), the spacing between this rotor element and the following rotor element increases to the maximum.

During movement of the respective rotor elements, the respective suction members each having at least one end pivotally supported on the associated rotor element are displaced around said ends laterally relative to the direction in which the rotor elements are rotated. The severed piece of elastic band linearly held under suction effect on the surface of each said suction member is laterally displaced in unison with the associated suction member and transported to the position at which said spacing increases to the maximum (the position (5)).

The web is continuously fed by said web feeding means to the point at which said rotor elements rotate at the highest speed and the severed pieces of elastic band held by the suction members on said respective rotor elements are successively brought from one end thereof into contact with the web. The respective rotor elements are controlled so that the average linear speed of the arc-shaped outer surfaces thereof corresponds to the speed at which the web is transport at said point of the highest rotational speed and the pieces of elastic band are applied from one end thereof onto the web by adhesive applied thereon as said pieces of elastic band are successively brought into contact with said web. Said respective suction members are controlled by the suction distributor means adapted to operate synchronously with rotation of said respective rotor elements caused by rotation of the drive wheel so that these suction members can be effective only within a range of their movement defined between a point immediately before the position at which the continuous elastic band comes into contact with said respective rotor elements (the position (1)) and the position at which the web comes into tangential contact with said respective rotor elements (the position (5)). Accordingly, the piece of elastic band which has been bonded onto the web at said position ⑤ is simultaneously relieved from the suction force of the associated suction member and effectively transferred onto said wet. The transfer of the elastic band onto said web occurs while said respective suction members maintain at least their one ends displaced, so one ends of said respective pieces of elastic band located on the previously mentioned one ends of the respective suction members are obliquely displaced relative to the direction in which said respective suction members rotate when bonded onto the web.

The various mechanisms are constructed and operated synchronously with one another so that the spacing developed between each rotor element and the following rotor element when the preceding rotor element reaches said position ⑤ corresponds to the spacing between each pair of adjacent pieces of elastic band bonded onto the web, and thereby said pieces of elastic band can be successively bonded onto the web at predetermined intervals.

The rotor elements which have completed said operation of transfer are now decelerated and moved from said position ⑤ to said position ①. In this course of movement, said respective suction members which have been laterally displaced restores again their linearly aligned orientation in the rotational direction and the operation as has been described above is repeated.

As will be readily apparent from the aforegoing description, according to the present invention, the continuous elastic band is severed into a predetermined length while it is held, the severed length of elastic band is transported along a circumferential path, said piece of elastic band is at least partially displaced laterally of the moving web while said circumferential path is maintained, then said piece of elastic band is further transported at a progressively accelerated speed to the position at which the continuous web is tangentially brought into contact with said piece of elastic band, and said piece of elastic band is transferred onto said web under synchronization of the elastic band transporting speed and the web feeding speed. Thus, the severed piece of elastic band may be progressively accelerated to widen the spacing between this piece of elastic band and the following elastic band to the maximum which corresponds to the spacing between each pair of adjacent pieces of elastic band intermittently applied onto the web. Furthermore, it is also possible, if desired, to successively apply the pieces of elastic band each severed into a predetermined length and curved into a predetermined orientation onto the web.

According to the important features of the present invention, severance, spacing adjustment and lateral displacement of the elastic band can be accomplished during its continuous movement along the circumferential path and applying of the elastic band can be performed by continuous operation, so the present invention can achieve not only speed-up and stabilization of the mechanism operation but also improvement of work efficiency all of which can not be expected from such method and apparatus of prior art.

It should be understood that, when said pieces of elastic band are to be applied onto the web merely in parallel, said suction members may be constructed so as to be not laterally displaced.

PREFERRED EMBODIMENT OF THE INVENTION

A preferred embodiment of the present invention will be described in reference with the accompanying drawing and with respect to a disposable diaper, by way of example.

Figures 1, 2:
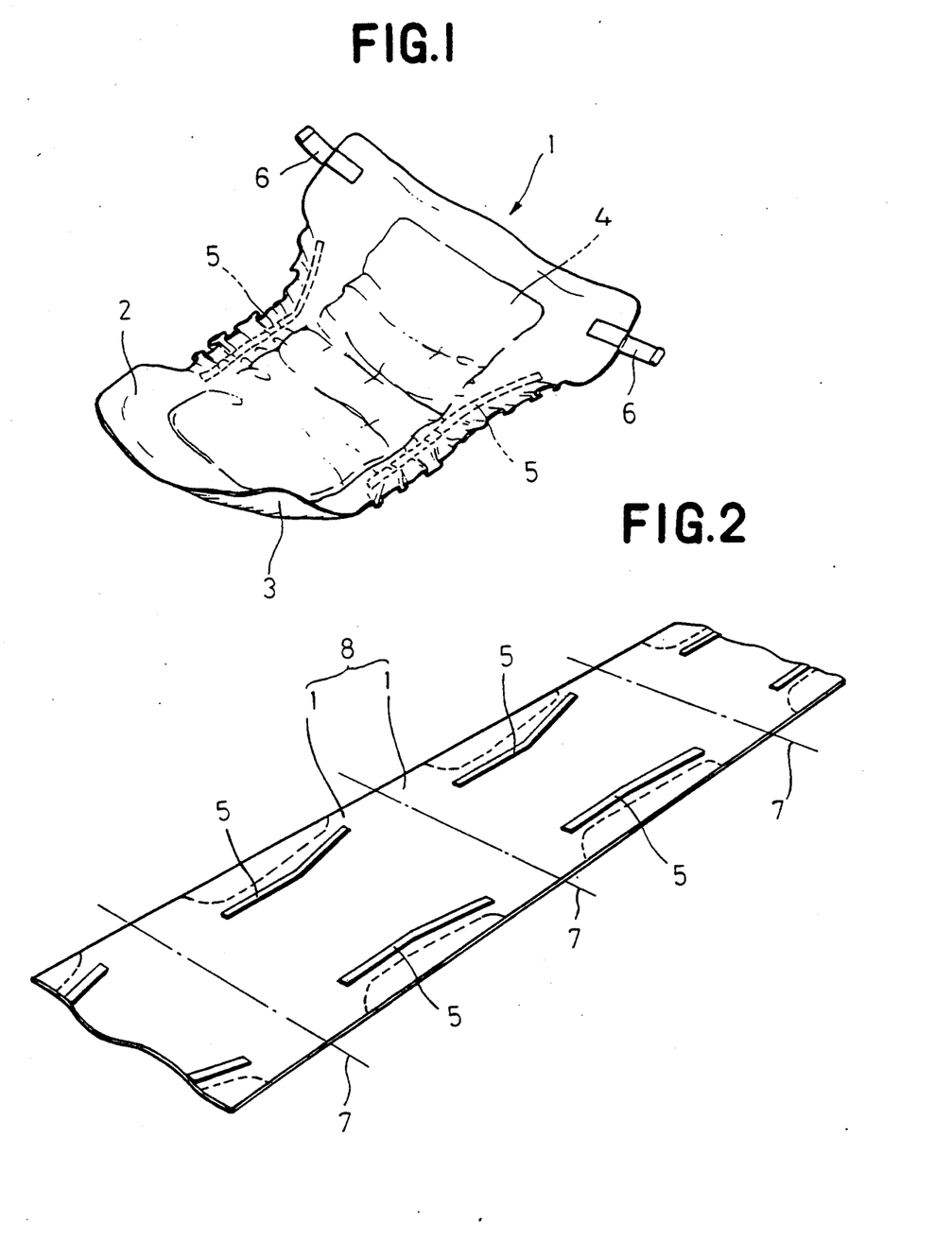
FIG. 1 is a perspective view showing an individual disposable diaper as a specific example of the article worked in accordance with the present invention.
FIG. 2 is a perspective view showing, by way of example, a manner in which pieces of elastic band are arranged on web as a primary component of said diaper at predetermined intervals.

Referring to FIG. 1, a diaper itself 1 comprises a water-permeable topsheet 2, a water-impermeable backsheet 3 and an absorptive core 4 interposed between said sheets 2 and 3. Ribbon- or tape-like pieces 5 of elastic band are respectively bonded, while they are maintained longitudinally stretched, onto opposite side flaps of the diaper itself 1 and so oriented that lengths of the respective pieces of elastic band 5 extending into an area corresponding to the user's hip are turned or curved obliquely outwards. One of opposite waist band portions of the diaper itself 1 is provided at laterally opposite ends with tape fasteners 6 adapted to be temporarily bonded to the other waist band portion to assemble the diaper when the latter is put on the user.

As shown by FIG. 2, continuous web 8, which is a primary component of said diaper itself 1 and will be eventually severed along respective broken lines 7 as shown into the backsheets or the topsheets, is provided on opposite sides thereof with the pieces 5 of elastic band, wherein said pieces 5 of elastic band are bonded onto said web 8 at predetermined intervals while these pieces 5 of elastic band are maintained longitudinally stretched, with the individual pieces 5 of elastic band being partially turned or curved obliquely outwards. Areas on opposite sides of each diaper itself 1 defined by broken lines shown are cut away to achieve the final configuration as shown by FIG. 1.

Figure 3:
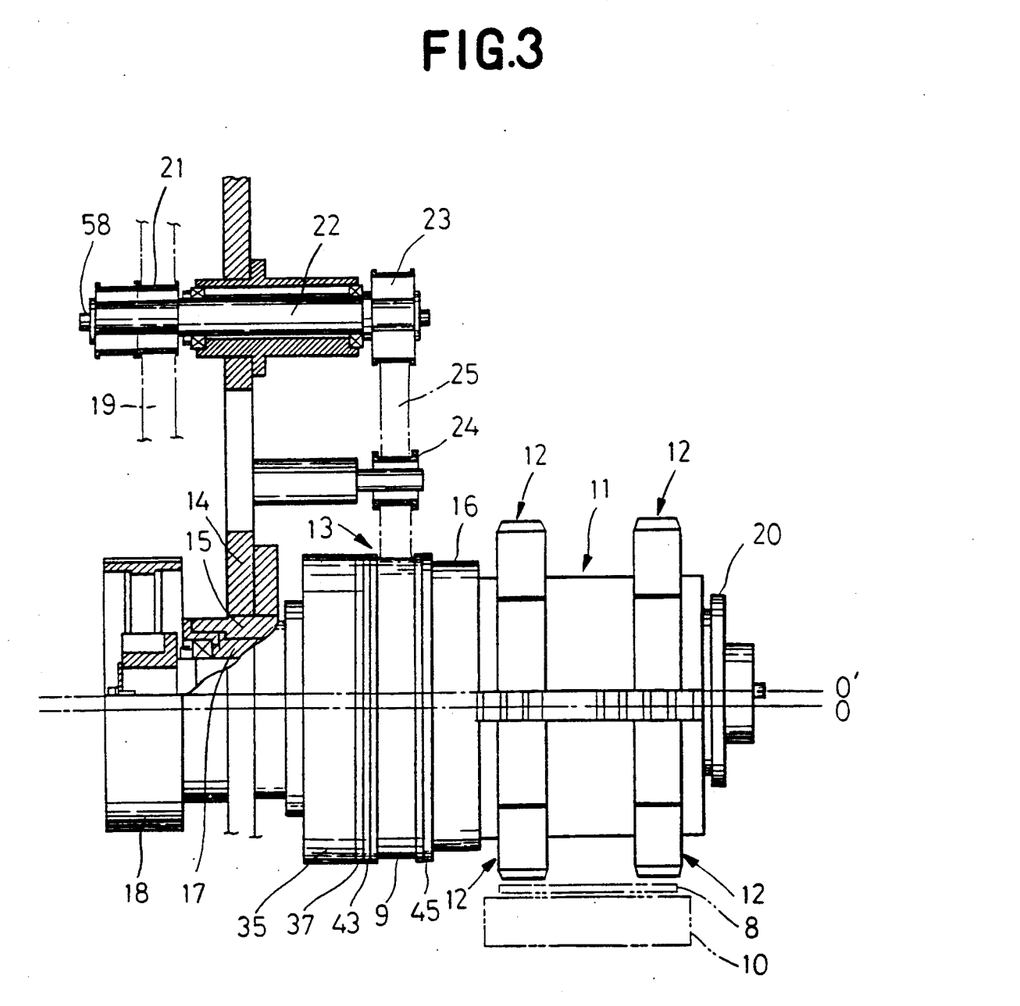
FIG. 3 is a side view partially broken away showing an embodiment of the apparatus constructed according to the present invention.

FIG. 3 shows an apparatus constructed in accordance with the present invention to be used for bonding said pieces of elastic band onto said continuous web 8. In a path along which the web 8 is transported under a tension by its transport means (not shown), there are provided rotatable elastic band transfer means 11 disposed to cooperate with a support roller 10 to hold the pieces 5 of elastic band and having on its arc-shaped outer surface circumferentially long arc-shaped suction members 12 and suction distributor means 13 for said suction members 11, both of which are rotatably supported by a tubular shaft 15 which is, in turn, secured to a side plate 14 on a stationary part of the apparatus. The suction members 12 are coupled to the suction distributor means 13 via an annular coupler 16 having a communication bore therethrough. Said annular coupler 16 will be described later in detail. A rotatable shaft 17 having an axis 0' offset to an axis 0 of the tubular shaft 15 extending through said tubular shaft 15. The rotatable shaft 17 is rotated at a constant speed by a belt 19 put on a pulley 18 affixed to one end of said rotatable shaft 17, and a drive wheel 20 affixed to the other end of said rotatable shaft 17 is coupled to the elastic band transfer means 11 for rotatably driving said transfer means. Said belt 19 is also put on a pulley 21 affixed around one end of a rotation transmitting shaft 22. The suction distributor means 13 is rotated by a transmission system at a constant speed in synchronization with the rotation of the elastic band transfer means 11 caused by the drive wheel 20, wherein said transmission system comprises a belt 25 traveling under guiding action of a free wheel 24 between a pulley 23 affixed to the other end of said rotation transmitting shaft 22 and the suction distributor means.

Figure 4:
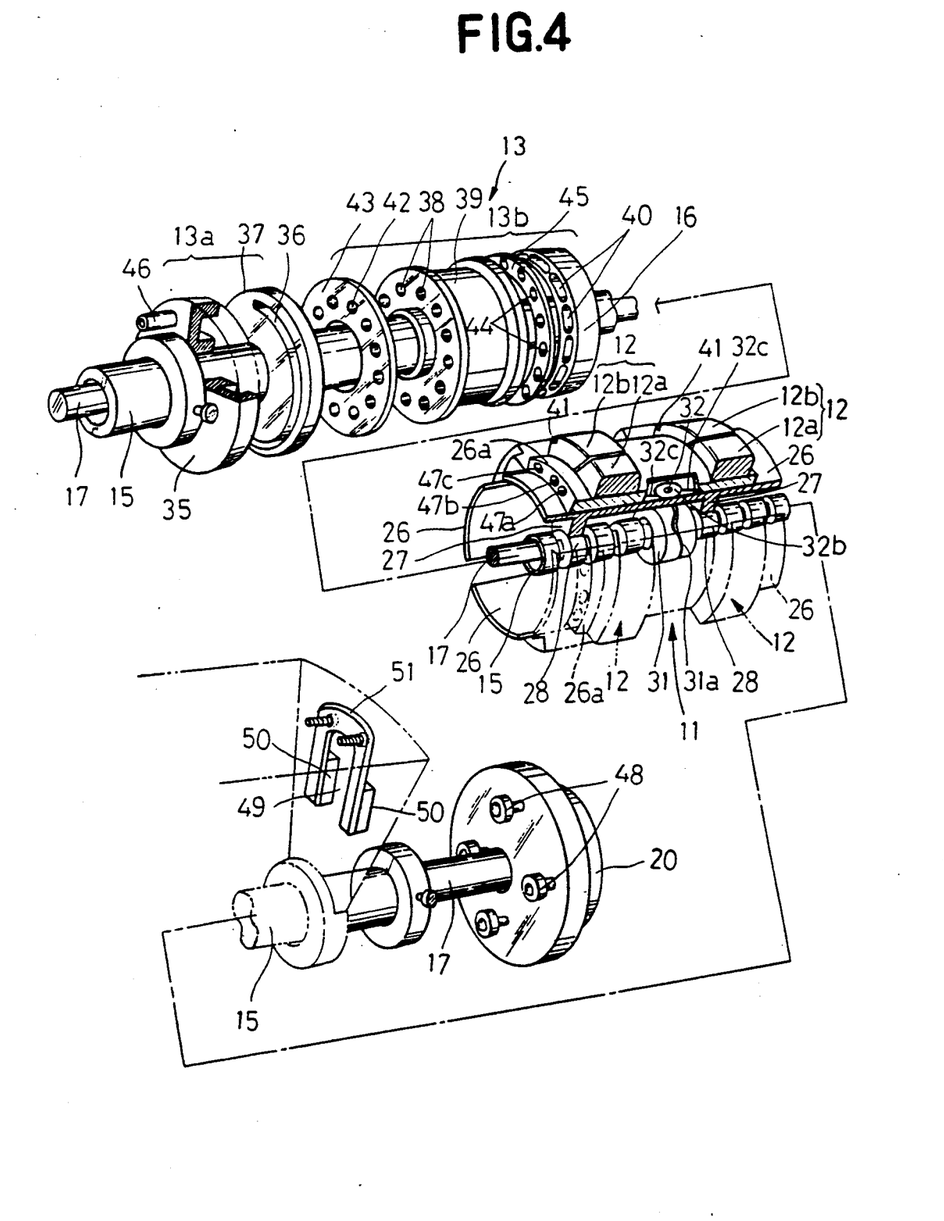
FIG. 4 is a fragmentary exploded perspective view partially broken away showing main parts of said embodiment in an enlarged scale.

Referring to FIG. 4, the elastic band transfer means 11 comprises four rotor elements 26 each having arc-shaped outer surface These rotor elements 26 are assembled into a single cylinder with opposite legs 27 of the respective U-shaped cross-sections being alternately laid one on another in the direction of the tubular shaft 15 and said arc-shaped outer surfaces of the respective rotor elements 26 are so dimensioned that the respective arc-shaped outer surfaces are separated by appropriate gaps from one another after they have been assembled into said cylinder. Legs 27 are respectively provided at radially inner ends with bearing assemblies 28 which are then incorporated into the tubular shaft 15 so that the respective rotor elements 26 can be independently rotated. Base blocks 26a fixedly mounted on the respective rotor elements 26 and having arc-shaped outer surfaces are provided on their tops at opposite sides with the associated suction members 12 so that these suction members 12 may have a common rotation plane.

As shown by FIGS. 4 through 7, each of the suction members 12 is divided into, in the rotating direction thereof, a front piece 12a and a rear piece 12b which are normally maintained in a linear alignment in said rotating direction. However, said front piece 12a is so movably mounted on the associated base block 26a that a front end of said front piece 12a may be laterally displaced over the base block 26a by a mechanism as will be described later around a stud 34 supporting the front piece 12a at its rear end. More specifically, the tubular shaft 15 supporting the rotor elements 26 is provided at its intermediate position with a stationary ring 31 having a circumferential cam groove 31a into which an eccentric pin 32a (see FIG. 5) of a rotatable shaft 32 supported centrally in the associated base block 26a at its front portion is slidably engaged, and thereby the lateral displacement of the right and left front pieces 12a is regulated through an associated link 32c pivotally supported at one end in a periphery of an actuator piece 32b which is integral with said rotatable shaft 32. This rotatable shaft 32 is rotatably supported in a bearing 33 fit into an opening 29 formed through the associated base block 26a and the rotor elements 26 define at a position opposed to said opening 29 an opening 30 extending therethrough to receive a lower end of said rotatable shaft 32 including the eccentric pin 32a. The other piece 12b is provided at its rear end with a counterknife 41 (see FIG. 6) adapted to cooperate with a corresponding cutter knife (not shown).

Figure 6:
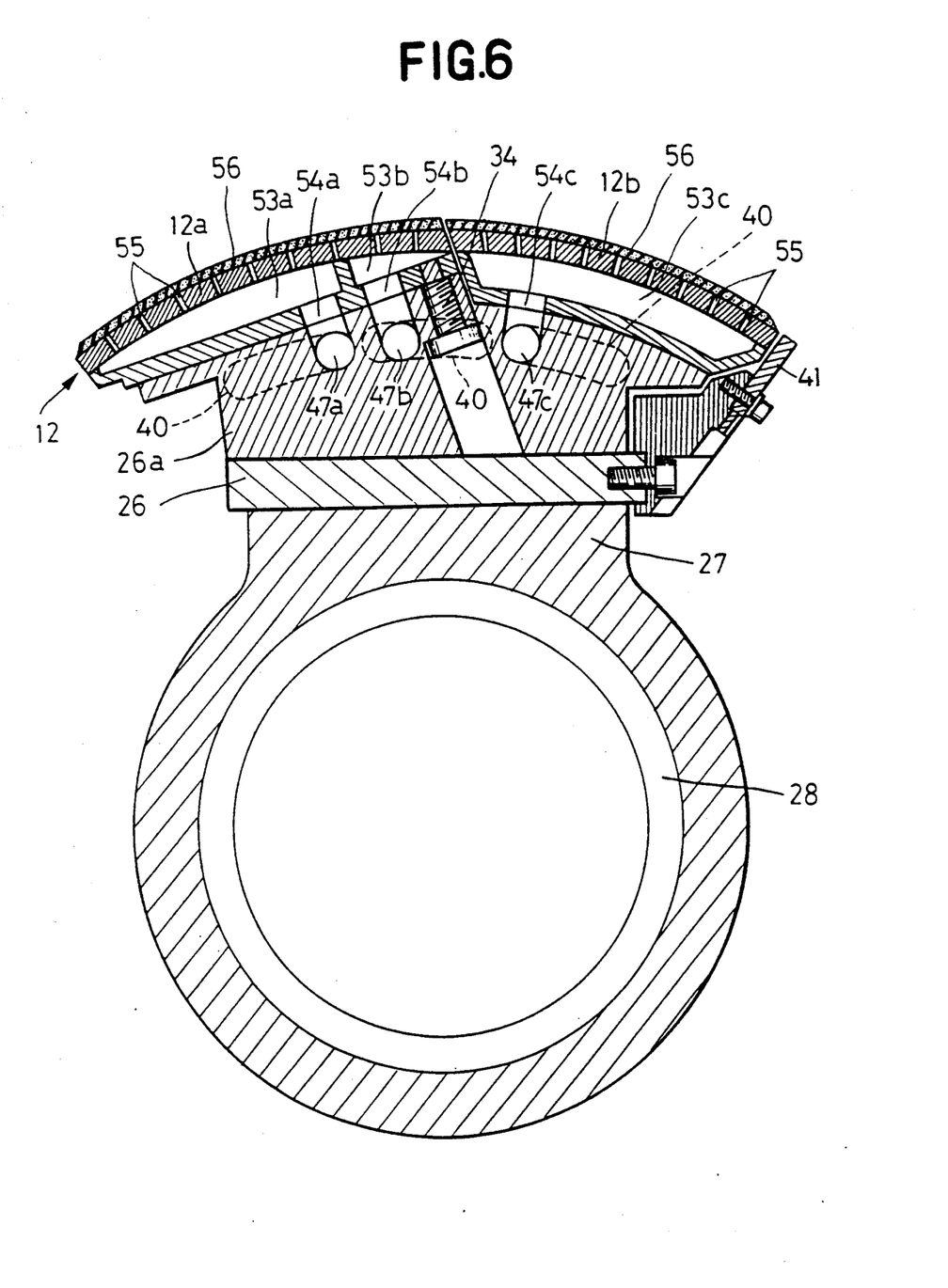
FIG. 6 is a vertical sectional view of rotor elements and suction members carried thereon included in said apparatus.
Figure 7:
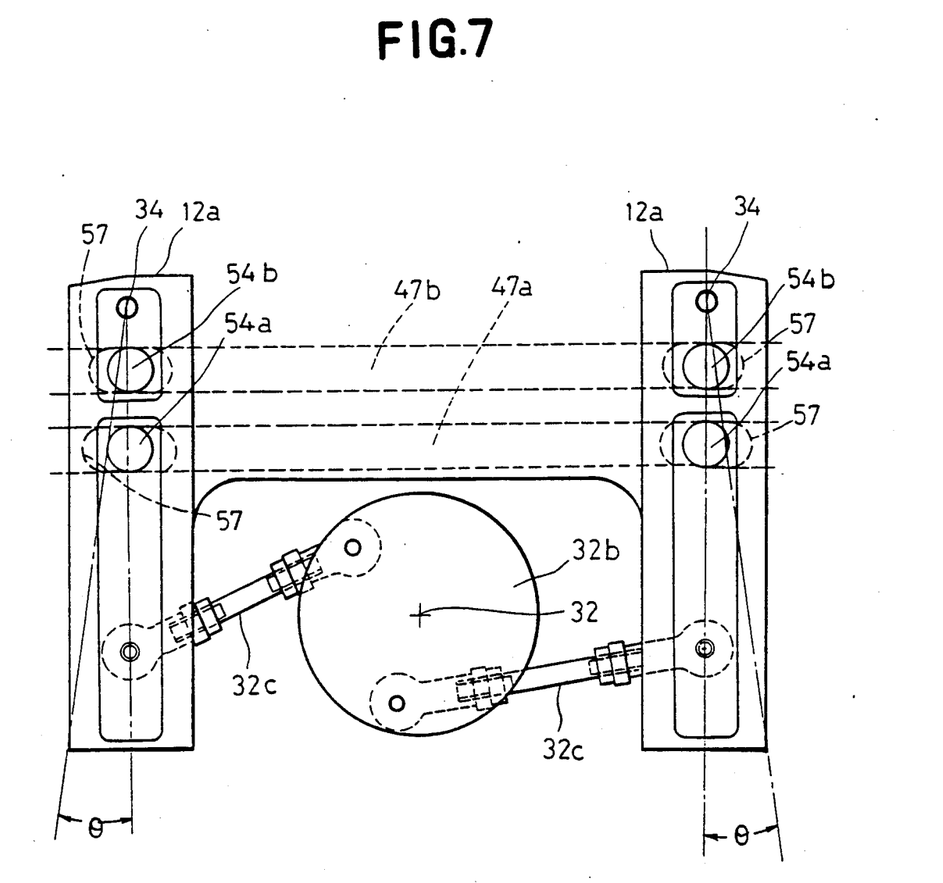
FIG. 7 is a plan view of a mechanism included in said apparatus for laterally displacing the pieces of elastic band.

The suction distributor means 13 comprises a stationary part 13a consisting of a stationary disc 35 fixed around the tubular shaft 15 and having a U-shaped cross-section on which a cover plate 37 having an arc-shaped suction port 36 slightly longer than a half of the circumferential range, and a rotatable part 13b consisting of a rotatable wheel 39 having its outer surface formed as a pulley surface and twelve ventilating holes 38 extending through its opposite side walls circumferentially at regular intervals; and the annular coupler 16 having arc-shaped ventilating holes 40 corresponding to said ventilating holes 38 but each dimensioned not to span each pair of adjacent said ventilating holes 38. The stationary part 13a and the rotatable part 13b are laid on each other with interposition of a slidable contact disc 43 having ventilating holes 42 corresponding to both said ventilating holes 38, 40 and a connector disc 45 having ventilating holes 44 similar to those of said slidable contact disc 43 so that, when suction is effected by an external suction pump (not shown) through a suction pipe 46 mounted through the stationary disc 35, only the ventilating holes 38 opposed to the suction port 36 define suction passages as the rotatable wheel 39 is rotated. The base block 26a contains three ventilating holes 47a, 47b, 47c axially extending therethrough transversely of the associated suction member 12 including both the front piece 12a and the rear piece 12b, and these ventilating holes 47a, 47b, 47c laterally open in the surface of this base block 26a that bears against the annular coupler 16. In this manner, the ventilating holes 47a, 47b, 47c for each suction member 12 correspond to and communicate with the ventilating holes 40 which, in turn, respectively correspond to the ventilating holes 38. Additionally, as shown in FIG. 6, there are provided ventilating holes 54a, 54b, 54c connecting cavities 53a, 53b, 53c in the pieces 12a, 12b of the suction member 12 to said ventilating holes 47a, 47b, 47c, respectively, and thereby desired suction occurs through a group of suction holes 55 formed in the surfaces of said pieces 12a, 12b and then through porous sheets 56 covering the respective pieces 12a, 12b. At transition to the ventilating holes 54a, 54b, 54c, openings 57 of said ventilating holes 47a, 47b, 47c are configured laterally long to accommodate the lateral displacement of the piece 12a.

Figure 5:
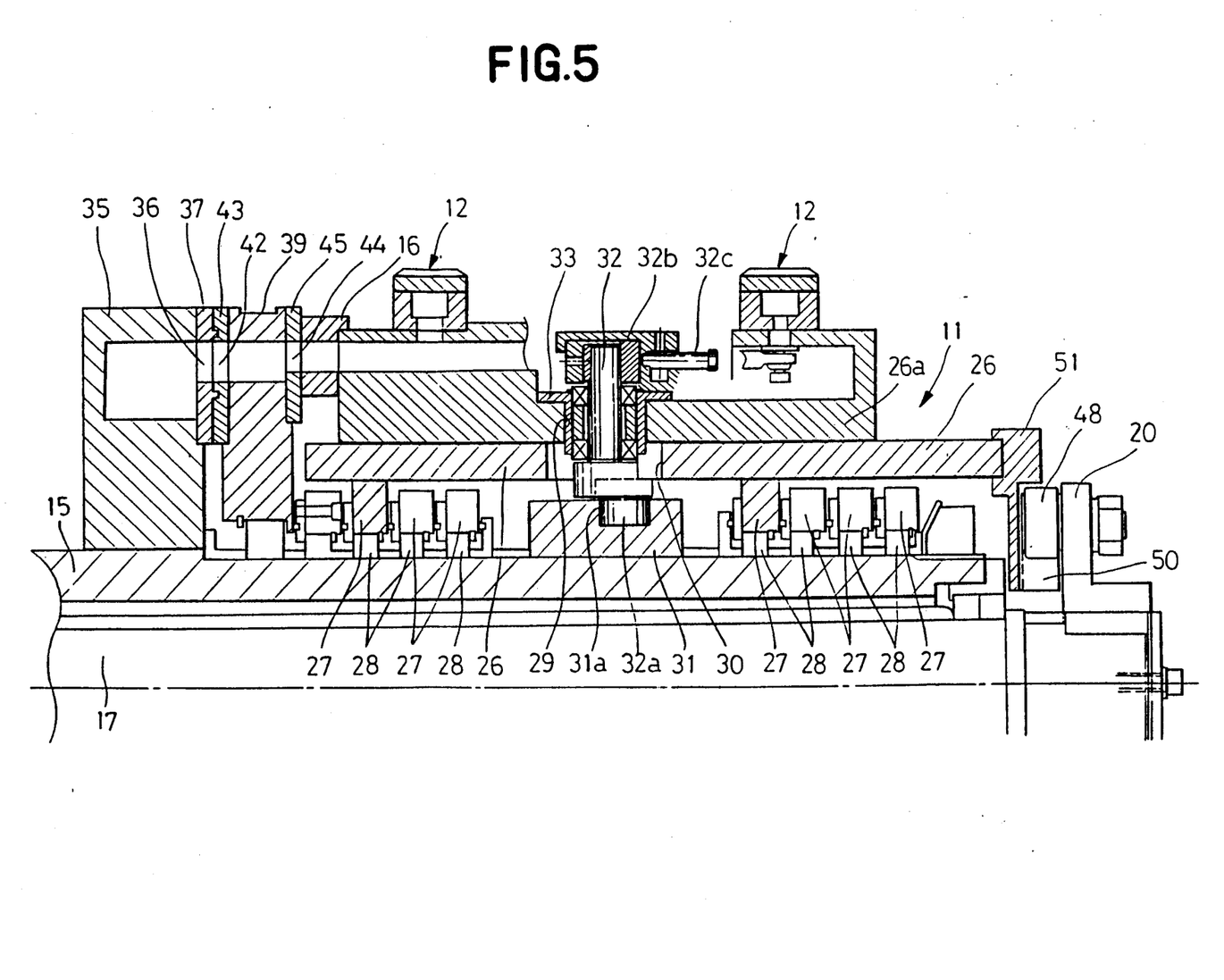
FIG. 5 is a sectional view showing said main parts as assembled together.
Figure 8:
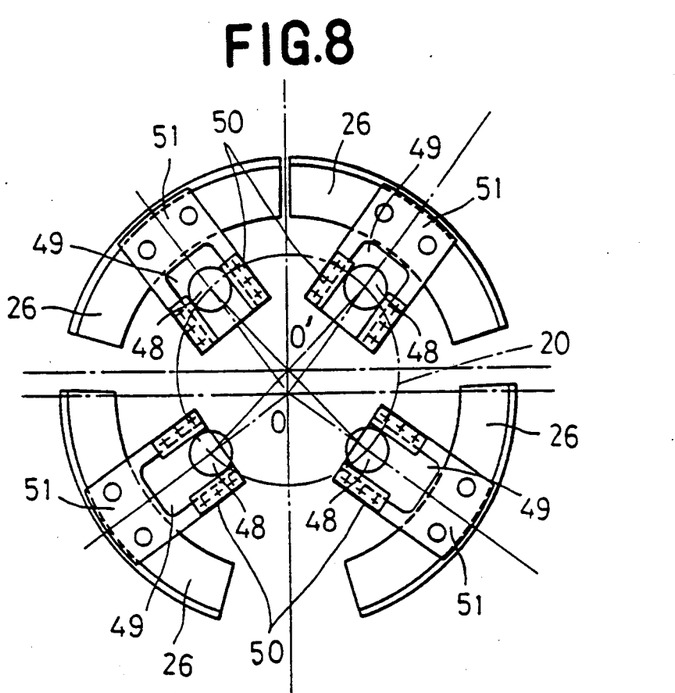
FIG. 8 is a side view of a rotor driving mechanism included in said apparatus.

As seen in FIGS. 4, 5 and 8, the drive wheel 20 includes four slidable engaging pins 48 projecting from and arranged at regular intervals on a side wall of the elastic band transfer means 11. Correspondingly, each rotor element 26 is provided at a side wall with a U-shaped guide piece 51 secured thereto, which includes contact pieces 50 mounted on both legs of said U-shaped defining therebetween a guide groove 49 extending towards the rotational center so that the respective slidable engaging pins 48 may be slidably engaged with said contact pieces 50. The respective slidable engaging pins 48 may be thus slidably engaged with the respective guide pieces 51 to establish a rotatable slider crank mechanism.

Figure 9:
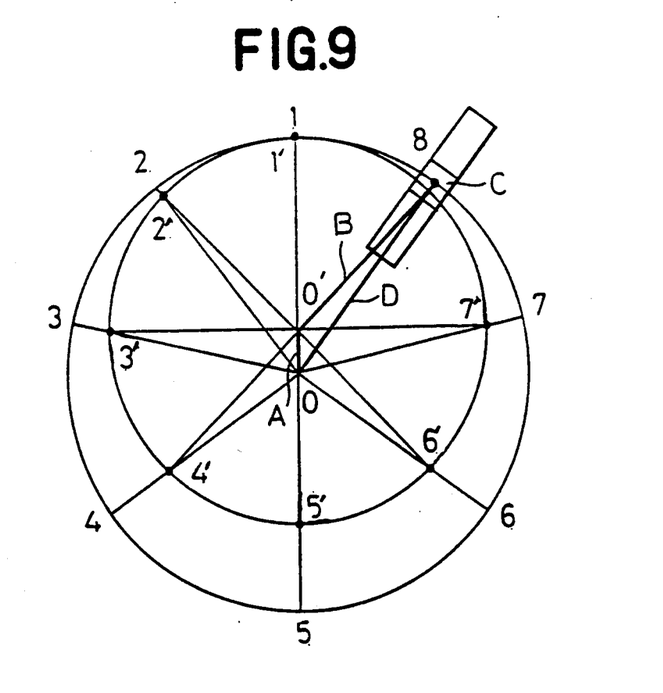
FIG. 9 is a diagram illustrating operation of a rotatable slider crank mechanism employed in said apparatus.

Now, operation of said rotatable slider crank mechanism will be considered in reference with FIGS. 8 and 9. Assumed that a link A is defined between a rotational center O of each rotor element 26 and a rotational center O' of the drive wheel 20 while a link B is defined between a center of the slidably engaging pin 48 serving as a slider C and said center O', a link D is defined between a center of the slidable engaging pin 48 with respect to the direction of the guide groove 49 and said center O. Thus, the respective rotor elements 26 are independently rotated at a variable speed, following a common rotational path, as the respective slidable engaging pins 48 of the drive wheel 20 are rotated at a constant speed. As a result, each pair of adjacent rotor elements 26 take a relative position at which they are most close to each other or even brought into contact with each other (top position in FIG. 8 or a position ① in FIG. 9) as they are rotated at a lower speed and take a relative position at which they are most widely spaced from each other (bottom position in FIG. 8 or a position ⑤ in FIG. 9) as they are rotated at a higher speed. The continuous elastic band (not shown) is fed in circumferential contact with said suction members 12 carried by said pair of adjacent rotor elements 26 to the relative position thereof at which these two rotor elements 26 are most close to each other.

Figure 10:
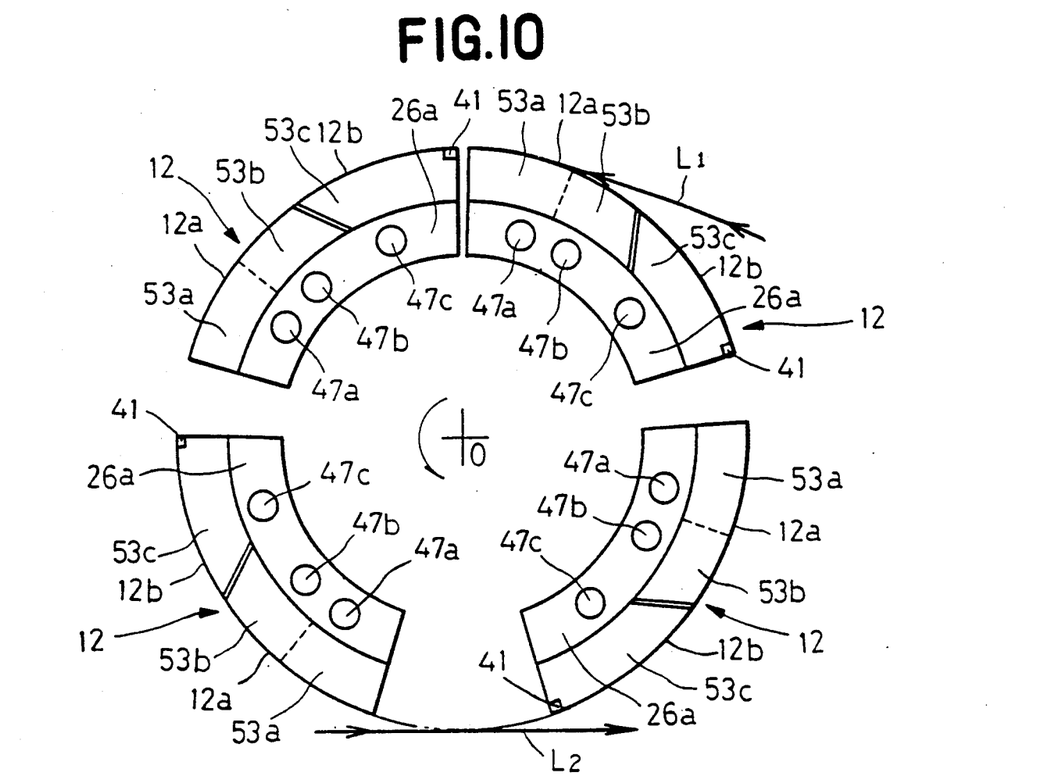
FIGS. 10 and 11 are diagrams simulatively illustrating how the pieces of elastic band are held by the suction members and how the suction effect is distributed in said apparatus.
Figure 11:
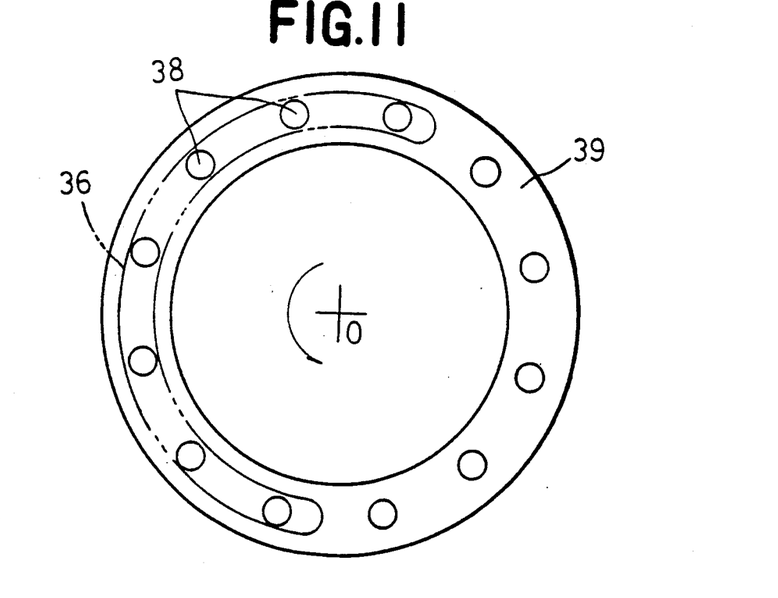

FIGS. 10 and 11 simulatively illustrate the respective suction members 12 carried by said respective rotor elements 26 and how suction is distributed among them. Assumed that the pieces 12a, 12b of each suction member 12 are linearly aligned in the rotational direction and the respective ventilating holes 38 of the rotatable wheel 39 communicating through the respective ventilating holes 40 of said annular coupler 16 with the ventilating holes 47a, 47b which are, in turn, in communication with the cavities 53a, 53b of the piece 12a as well as with the ventilating hole 47c which is, in turn, in communication with the cavity 53c of the piece 12b take their positions as shown in FIG. 11, the suction port 36 of said cover plate 37 facing the rotatable wheel 39 will be positioned as shown by a broken line. Accordingly, the ventilating holes 47a, 47b, 47c of the left upper suction member 12 (consisting of the left and right suction pieces) and the ventilating hole 47a of the following, that is, the right upper suction member 12 (consisting of the left and right suction pieces) are subjected to the suction effect and an area including these particular holes is effective to provide a suction force. In such a situation, the continuous elastic band being maintained in a stretched condition is tangentially fed as indicated by a line $L_1$ in FIG. 10 and severed on the left upper suction member 12 positioned as shown by FIG. 10, as the cutter knife (not shown) operating synchronously with the counterknife 41 carried by said suction member 12 comes into cooperation with the counterknife. Thus, a piece of the elastic band severed into a predetermined length corresponding to an arc length defined by the effective suction area of said suction member 12 is held thereon under the suction effect during rotation of said suction member 12. Immediately after said left upper suction member 12 has been rotated together with the rotating wheel 39 in the direction as indicated by an arrow, the ventilating hole 47b of said right upper suction member 12 now communicates with the ventilating holes 38 which have newly entered into the area of the suction port 36 and said right upper suction member 12 holds thereon under the suction effect said continuous elastic band which continues to be fed, while the ventilating hole 47a of the left lower suction member 12 in FIG. 10 communicating with the ventilating holes 38 which are now out of the area defined by the suction port 36 loses its suction force acting upon a portion of said severed piece of elastic band (corresponding to the front portion of the piece 12). The eccentric pin 32a of said rotatable shaft 32 is guided by the cam groove 31a as each rotor element 26 is rotated and thereby the actuator piece 32b of the rotatable shaft 32 is counterclockwise rotated as viewed in FIG. 7. This causes the link 32c to displace said piece 12a around its supporting stud 34 outwards by a displacement angle of $\theta$ (approximately 8° at the maximum). The previously mentioned continuous web (see FIG. 2) is tangentially fed to the position at which each pair of adjacent rotor elements 26 are most widely spaced and angularly displaced from each other, namely, at which the ventilating hole 47a of the suction member 12 loses its suction force, in the direction as indicated by a line $L_2$ in FIG. 10. The severed piece of the elastic band held by the suction member 12 is bonded with adhesive applied on this severed piece of elastic band onto said web which is controlled to be transported at a speed corresponding to the average speed at which the suction member 12 has traveled to said position. Then, said severed piece of elastic band is transferred from the suction member 12 now having no effective suction force onto said web. As the respective rotor elements 26 continue to be rotated, the pieces of elastic band held and severed on the respective suction members are successively transferred from the forward ends of the respective pieces of elastic band onto said web being transported, wherein the previously mentioned rotatable slider crank mechanism presets the maximum spacing between each pair of adjacent rotor elements 26 to a distance by which each pair of adjacent pieces of elastic band should be spaced from each other on the web so that the respective pieces of elastic band may be transferred onto the web 8 at predetermined intervals, as seen in FIG. 2.

As the rotor elements 26 continuously rotating after completion of said transfer operation is decelerated under control of said rotatable slider crank mechanism so as to reduce said spacing, the piece 12a of each suction member 12 is returned, under control of said cam groove 31a, to the initial linear alignment.

The drive mechanism of such apparatus can employ as its input means various arrangements such as a power shaft (not shown) and a pulley 58 (see FIG. 3) on which a belt is put.

In a case where it is unnecessary for the suction member 12 to be laterally displaced by a given angle, it is unnecessary not only to divide said suction member 12 into two pieces 12a, 12b but also to employ means by which any one of said pieces is displaced through a cam mechanism.

The elastic band transfer means 11 may be constituted by two rotor elements 26 and these rotor elements may be most preferably driven by the rotatable slider crank mechanism as in the embodiment as described and illustrated. However, this mechanism may be replaced by the other types of crank mechanism or a cam mechanism. Further, the suction member 12, if it is desired to displace it by a given angle, may be controlled by a suitable mechanism such as cam mechanism or crank mechanism so that both the pieces 12a, 12b are laterally displaced by given angles or the suction member 12, without dividing it into said two pieces, is laterally displaced by a given angle.

What is claimed is:

1. Apparatus for intermittently severing two continuous bands of elastic into a series of pieces (5) of predetermined length and thereafter applying these pieces (5) to a moving continuous web (1) in spaced apart relationship to each other, said apparatus comprising in combination
    (a) a plurality of separate but circumferentially aligned rotor elements (26, 26a) that are sequentially spaced apart and rotatably supported by a first shaft (15) about an axis 0,
    (b) each rotor element (26, 226a) being provided with at least two suction members (12) having arc-shaped outer surfaces that are laterally spaced from each other, each suction member (12) being adapted to hold one piece (5) of said elastic band against its arc-shaped outer surface,
    (c) suction distributor means (13) associated with said suction members (12) to alternately apply suction and release suction from said suction members 12,
    (d) a drive wheel (20) mounted on a second shaft having an axis 0' that is offset from the 0 axis of said first shaft (15),
    (e) each rotor element (26, 26a) having a side wall that is provided with guide piece (49-51) and the drive wheel (20) being provided with a number of slidable engaging pins (48), each engaging pin (48) slidably engaging with a guide piece (49-51) whereby when the drive wheel (20) is rotated at constant speed the rotor elements (20, 26) are independently rotated at a variable speed following a common rotational path with the result that each pair of adjacent rotor elements (20, 26) are alternately moved close to each other and then farther apart from each other,
    (f) means to separately feed each of said two continuous elastic bands against the outer arcuate surfaces of said suction members (12),
    (g) severing means (41) intermittently cooperating with said suction members (12) to sever said continuous elastic band into pieces (5), and
    (h) web feeding means (10) located near the rotational path of said suction members (12) for transferring each severed piece (5) of elastic band to said continuous web (1).

2. An apparatus according to claim 1 wherein each suction member (12) is composed of two sections (12a, 12b) and means are provided for moving one section laterally with respect to the other.

3. Apparatus as recited in claim 1 wherein said suction distributor means (13) includes a stationary disc having a circumferentially long arc-shaped suction port and a rotatable wheel having a plurality of ventilating holes circumferentially arranged at regular intervals in concentric relationship with said suction port and said respective ventilating holes are in communication with said respective suction members.

4. Apparatus as recited in claim 2 wherein said means for laterally moving said one section includes a cam mechanism.

* * * * *